(12) United States Patent
de la Torre-Bueno

(10) Patent No.: US 7,970,197 B2
(45) Date of Patent: Jun. 28, 2011

(54) SYSTEM AND METHOD FOR PREVENTING SAMPLE MISIDENTIFICATION IN PATHOLOGY LABORATORIES

(75) Inventor: Jose de la Torre-Bueno, Vista, CA (US)

(73) Assignee: Clarient, Inc., Aliso Viejo, CA (US)

( * ) Notice: Subject to any disclaimer, the term of this patent is extended or adjusted under 35 U.S.C. 154(b) by 910 days.

(21) Appl. No.: 11/930,028

(22) Filed: Oct. 30, 2007

(65) Prior Publication Data

US 2009/0110253 A1  Apr. 30, 2009

(51) Int. Cl.
*G06K 9/00* (2006.01)

(52) U.S. Cl. ............................. 382/133; 348/79; 378/43

(58) Field of Classification Search .................. 382/100, 382/128, 133, 134; 377/10, 11; 378/43; 348/79

See application file for complete search history.

(56) References Cited

U.S. PATENT DOCUMENTS

| | | | | |
|---|---|---|---|---|
| 5,671,288 | A  * | 9/1997 | Wilhelm et al. | 382/128 |
| 7,006,674 | B1 * | 2/2006 | Zahniser et al. | 382/128 |
| 2006/0015262 | A1 * | 1/2006 | Gholap et al. | 702/19 |
| 2006/0104499 | A1 * | 5/2006 | Zahniser et al. | 382/141 |
| 2009/0214088 | A1 * | 8/2009 | Sorenson et al. | 382/128 |

* cited by examiner

*Primary Examiner* — Anand Bhatnagar
(74) *Attorney, Agent, or Firm* — Fish & Associates, PC

(57) ABSTRACT

A block of tissue is imaged and used as a reference. Later slides formed from that tissue receive numbers, and are also imaged. The imaged slides are compared to the reference image to determine identification errors.

13 Claims, 2 Drawing Sheets

SYSTEM AND METHOD FOR PREVENTING SAMPLE MISIDENTIFICATION IN PATHOLOGY LABORATORIES

BACKGROUND

Large anatomic pathology laboratories may receive hundreds of specimens each day. For example, the slides can be blocks of paraffin embedded tissue. The laboratories can prepare thousands of slides from those blocks. Any slide that becomes misidentified creates a potential for misdiagnosis.

The original sample received by the lab, referred to herein as "the block" is used to create new samples. Hence, the tracking system takes into account the parent-child relationship among the samples.

Because any misidentification can cause a misdiagnosis, pathology laboratories must take great care in labeling the slides. Typically this is done at the time the block is sectioned to make the slides. However, many devices used in the laboratory, such as autostainers, require special codes, e.g., barcodes to work with a slide. Because of this, it may be necessary to re-barcode the slides several times over the course of the workflow.

SUMMARY

The inventor recognized that each time an identifying marker, e.g. a barcode, is first affixed and each time a new identifying marker, e.g., another barcode is later affixed, forms a potential opportunity for human error. The problem is exacerbated by the fact that some of the solvents involved in the staining process are harsh enough to remove some types of identifying markers, e.g., by removing labels, or erasing ink.

An embodiment describes an automated technique of checking samples against a stored sample in a database.

According to an embodiment, a sample is first identified, and stored in a database along with identifying information. Later, slides which have been taken from that sample are compared with the information in the database. If the slides do not match the image in the database, they are flagged as being in error and may be relabeled or otherwise processed.

DETAILED DESCRIPTION

Currently no fully satisfactory solution exists for the problem of mislabeled slides. Engraving the slides with a permanent label before placing the specimen may prevent the loss of label problem but still requires human care to attach the correct specimen to the pre-labeled slide.

Further the auxiliary labels required for other processes will need to be added over the engraved label; and later a new label with the same information that was engraved applied over the auxiliary label(s).

In general, the laboratory can reduce this misidentification problem by training and repeated double checks by extra people.

The shape of the specimen on the slide might be used as a double-check in some circumstances. When multiple slides are made from a block, the sections that are cut on a microtome are typically serial sections. This means that each is a thin (5 microns typically) slice of the block. Each succeeding section is cut from the very next layer of the block. The embedded tissue changes very little in the space of 5 microns. Hence, the outer shapes of the sections on all the slides have similar sizes and shapes.

The sections are captured on the surface of a water bath and then transferred onto the slide. Therefore, the similar shapes may end up in different positions on the slide. However, the similarity of 2 serial sections will be apparent despite any rotation and translation relative to each other.

Well trained technicians in a laboratory may use this similarity as a secondary check that all the slides that are associated with a case came from the same block. In some laboratories, the slides are carried in trays that hold all the slides face up over a white background. If the laboratory consistently handles slides by case, the technician can look at the tray and check that the slides all have tissue with the same basic shape on them.

This manual technique has shortcomings. Among them are:

The slides in a case can come from 2 or more blocks which makes comparison a much more tedious process.

When the sample is a needle biopsy, the shape of the sample is determined by the size and shape of the needle. Slides from needle biopsies may not be as easy to tell apart as randomly shaped surgical samples.

When all the slides in a case are together, it is easy to compare them and notice if one seems to be from a different block. However, during the lab workflow, it is often necessary to separate the slides from a given case. For instance, slides often go on different autostainers to be processed with different reagents. When different slides go to different machines, the comparison of slides from one case can no longer be used to identify a mislabeled slide unless the slides are reassembled by case as they come off each machine.

An embodiment addresses these problems by using cameras and analysis software to image the block when it is first received and to check that image against images of the tissue on the slides at various steps in the workflow.

Figure 1:
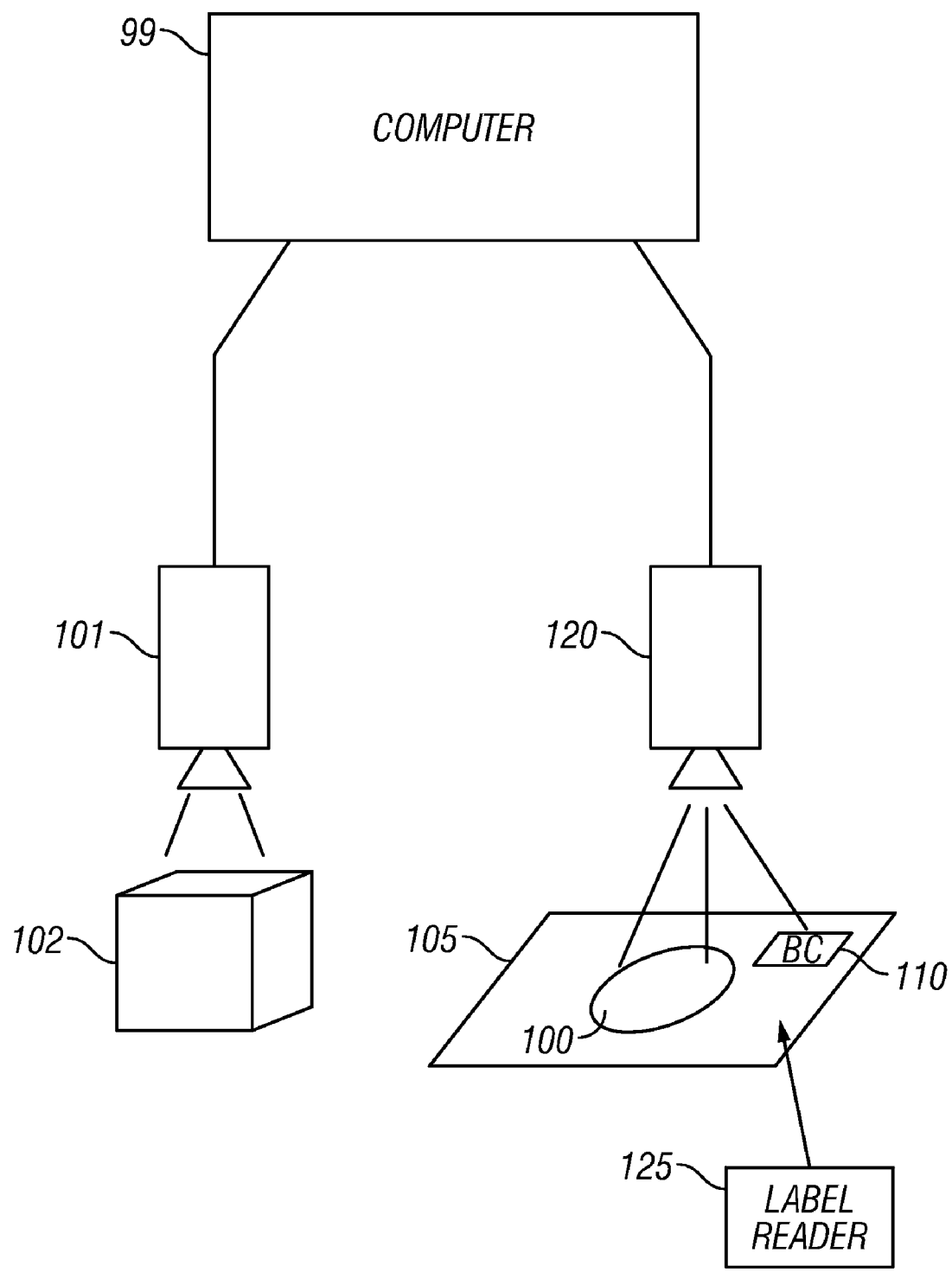
FIG. 1 shows a block diagram.
Figure 2:
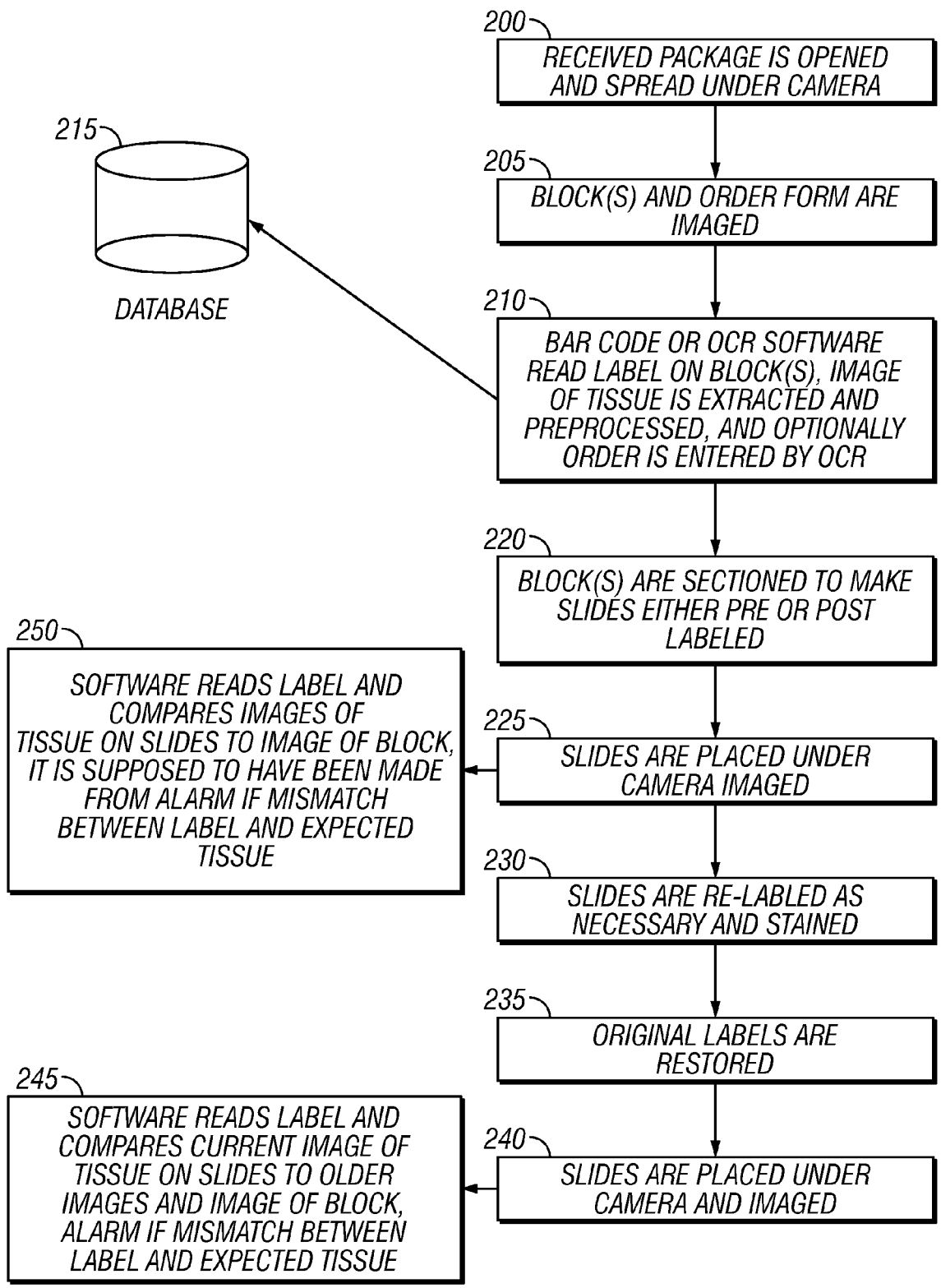
FIG. 2 shows a flow diagram.

An embodiment is shown in FIG. 1, and a flow diagram of the process is shown in FIG. 2.

In the embodiment, the block 102 is first imaged by imager 101. The block may be associated with an order number. The image of the block 102, and the order number, are both stored in computer 99.

Later, the block is sectioned, to form tissue 100 which is placed on a slide 105, which also includes a label 110 thereon. An imager 120 obtains an image of the tissue viewed at a scale in which the whole active region of the slide is visible. The imager 120 may be the same as 101, or may be separate as shown.

The camera can also image the label 110, or there can alternatively be a label reader 125.

That image of the tissue 100 is compared with at least one other image, e.g. of the block 102, as stored in computer 99. Other images that can be used for the comparing include the image of the tissue on the original block 99 and/or with the image collected from a slide earlier and/or the images of the tissue on other slides from the same block.

A match criterion is established. A failure of the images to match by the amount of the match criterion is used to signify a warning that the expected tissue as indicated by the label is not the actual tissue on the slide. The match criterion, can be, for example, a 30% match. One explanation for a mismatch may be when the label is wrong.

The process shown in FIG. 2, first receives the package 200, e.g. the block 102, or one or more slides. These are imaged. at 205, where an imager, e.g., 101, takes an image of the package.

This image is associated with the order number, e.g., an order form on the slide at 210, e.g., the label on the slide is automatically detected, e.g. by reading the barcode, or OCRing the label on the block. The image of the tissue is also extracted, and preprocessed. The image and the order number may be stored in a database at 215 (which may be the computer 99 or a remote database), along with information about the image.

At 220, the blocks are then sectioned to make slides. The slides are labeled, either before or after this operation. At 225, the slides are placed under the imager 110 to obtain an image.

250 reads the label, and compares the images of tissue 100 on the slide to the images of the block as stored in the database. If the mismatch between these two parts is greater than a mismatch limit, e.g. 30%, then an alarm is raised. Responsive to the alarm being raised at 250, the slides may be relabeled at 230, and stained. Original slides may be re stored at 235, and imaged 240. At 245, the processing computer, e.g. 99, compares current images of the tissue on the slide to older images, e.g., images of the block.

The above described 205 imaging the "block" but it should be understood 205 could alternatively image other slides that were formed from the block, or something else from which the block can be identified.

An embodiment describes barcodes to determine slide identification. However, alternately, this could be used with any identification method including text read by OCR or RFID.

Hardware such as camera 120 to collect images of the necessary resolution is available commercially. The requirement is to image a region about 25×25 mm at a resolution such that the outline of the tissue on a slide can be resolved. Typically 128 resolution elements across a slide are sufficient, so a macro camera with 1024×1024 pixels could image a whole tray of slides at once. The disclosed resolution is not limiting, however, any image which has enough detail to compare the sections at a macro scale will be usable.

Camera 120 may be a camera mounted at a fixed height on a stand with lights. In pathology these are made for imaging tissue samples before they are dissected. Similar setups are manufactured for inspection and documentation in other industries. Maintaining the camera at a fixed known height has the advantage that the scale can be calculated. This may have algorithmic advantages, as described below.

Another type imager which can be used is a standard flatbed scanner, these also have the advantage of producing images of a known scale. Different imagers can be compensated by calibrating the relative scale. For example, all of the imagers can be made to show a reference object during setup time, and comparisons between the reference objects can be used to calibrate the imagers.

The image comparing at 250 can use any of a number of different image comparing techniques. The comparing technique preferably provides a result that indicates whether a satisfactory match was found and preferably is able to compensate for translational and rotational displacement of the tissue on the slide.

The latter requirement arises from the method used to put the tissue sections on the slide. Typically when a block is sectioned, the cut sections drop off the knife onto a water bath. The histologist then scoops the section out of the water bath onto the slide. Given this methodology, the histologist has only limited control of where on the slide the section adheres.

Based on this realization, the inventor realizes that any method used to compare serial sections between slides or between slides and the block must account for some translation or rotation. In the hands of a skilled histologist, the degree of offset should be limited but it is possible for a section to wind up 180 degree reversed or even upside down on a slide.

The knowledge of where the sample is on the block and earlier slides is still valuable in applying image matching algorithms because many algorithms of this type work better or faster if given a "hint" about where to start searching. These algorithms can also work faster if the degree of scaling can be restricted. In this application, this is possible if the images are collected with flatbed scanners or cameras fixed on stands so that the scale is constant for each camera and can be calculated. Note that the cameras do not have to have the same scale or resolution as long as the scale can be calculated since images from different cameras can be scaled before comparison.

Some examples of known techniques which are capable of carrying out the necessary pattern matching are described below without intent to limit the claims to these specific techniques. Any technique capable of generating a quantitative measure of a degree of match between two images (invariant over translation and rotation) could be used.

The commercially available image library MIL from Matrox has a "Geometric Model Finder" function which given a target image and an acquired image will find the target image in the acquired image even if it is translated and rotated. It will return a value indicating the reliability of the match as well as the measured displacement and rotation.

Another technique which is suitable for this method is as follows:

Binarize the 2 images to be compared with suitable thresholds (i.e. color or black and white thresholds that distinguish tissue from background). Note that if the objects compared are different colors, for instance a block compared to a stained slide, different thresholds would be needed.

Use blob analysis to get the size and centroid of each piece of tissue.

If the sizes differ by more than a preset criteria then there is no match; raise an alarm.

Otherwise for each image measure the distance from the centroid to the edge along a selection of angles. This will generate 2 functions of distance as a function of angle.

Cross correlate the 2 functions. The maximum magnitude of the cross correlation is a measure of how similar in shape the 2 objects are and the offset at which the maximum occurs is a measure of the rotation between the 2 images. If the measure of similarity is below a selected criteria (e.g., 30%) raise an alarm.

The above algorithm assumes that each shape is a convex hull. However, other modifications can be used such as using the most distant edge if 2 or more are encountered along a given angle, and/or adapting the algorithm to more complex shapes.

Regardless of the technique chosen, according to an embodiment, it may be important to use the unique shape of a given sample as a method of distinguishing the sample from other samples being processed at the same time.

The general structure and techniques, and more specific embodiments which can be used to effect different ways of carrying out the more general goals are described herein.

Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art. For example, other image comparison techniques, such as least mean squares comparisons between the images can be used.

Also, the inventor intends that only those claims which use the words "means for" are intended to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The computer may be an Intel (e.g., Pentium or Core 2 duo) or AMD based computer, running Windows XP or Linux, or may be a Macintosh computer. The computer may also be a handheld computer, such as a PDA, cellphone, or laptop.

The programs may be written in C or Python, or Java, Brew or any other programming language. The programs may be resident on a storage medium, e.g., magnetic or optical, e.g. the computer hard drive, a removable disk or media such as a memory stick or SD media, wired or wireless network based or Bluetooth based Network Attached Storage (NAS), or other removable medium or other removable medium. The programs may also be run over a network, for example, with a server or other machine sending signals to the local machine, which allows the local machine to carry out the operations described herein.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

What is claimed is:

1. A method, comprising:
   obtaining electronic information indicative of an image of a sample that includes tissue along with identifying information indicative of said sample;
   storing said electronic information in a storage unit along with said identifying information about said sample of tissue;
   forming at least one slide from said sample of tissue and forming identifying information on said slide;
   obtaining an image of tissue on said slide;
   using said identifying information from said slide to obtain a reference image from the storage unit, where said reference image from the storage unit is based on said identifying information and corresponds to information that is intended to be on said slide;
   using a computer for comparing said image of the tissue on said slide with said reference image from the storage unit; and
   responsive to said image of tissue on the slide differing from said reference image from the database, by more than a specified amount, flagging a mismatch slide.

2. A method as in claim 1, wherein said sample of tissue is a block of tissue from which slides are going to be obtained.

3. A method as in claim 1, wherein sample of tissue is a slide which has been previously obtained from a block of tissue.

4. A method as in claim 1, wherein said obtaining an image comprises using a camera.

5. A method as in claim 4, wherein said camera is maintained at a fixed distance from the slide in order to maintain a constant scale between said camera and said slide.

6. A method as in claim 1, further comprising maintaining a constant scale between said image of said sample of tissue, and said image of said tissue on said slide.

7. A method as in claim 1, wherein said obtaining an image comprises using a scanner.

8. A method as in claim 1, wherein said comparing comprises binarizing the reference image, binarizing the image of tissue on the slide, and using blob analysis to compare the images.

9. A method as in claim 8, further comprising determining functions of distance as a function of angle.

10. A method as in claim 1, wherein said obtaining an image of tissue on a slide comprises obtaining images of plural different slides all at the same time.

11. A method as in claim 1, further comprising responsive to said flagging a mismatch, forcing relabeling of said slide.

12. A method, comprising:
    obtaining electronic information indicative of an image of a sample that includes tissue along with identifying information indicative of said sample;
    storing said electronic information in a storage unit along with said identifying information about said sample of tissue;
    forming plural slides from said sample of tissue and forming identifying information on each of said plural slides;
    obtaining a single image that includes all the tissue on each of said slides;
    using said identifying information from said slides to obtain a reference image from the storage unit, where said reference image from the storage unit is based on said identifying information and corresponds to information that is intended to be on said slides;
    using a computer for comparing said images of the tissue on said slides with said reference image from the storage unit; and
    responsive to said image of tissue on any of the slides differing from said reference image from the database, by more than a specified amount, flagging a mismatch slide.

13. A method as in claim 12, further comprising responsive to said flagging a mismatch, forcing relabeling of said slide.

* * * * *